US008580308B2

(12) United States Patent
Heacock et al.

(10) Patent No.: US 8,580,308 B2
(45) Date of Patent: Nov. 12, 2013

(54) MODAFINIL PHARMACEUTICAL COMPOSITIONS

(75) Inventors: Craig Heacock, Downingtown, PA (US); Alpa Parikh, Avondale, PA (US); Piyush Patel, Wallingford, PA (US)

(73) Assignee: Cephalon, Inc., Frazer, PA (US)

( * ) Notice: Subject to any disclaimer, the term of this patent is extended or adjusted under 35 U.S.C. 154(b) by 397 days.

(21) Appl. No.: 11/550,588

(22) Filed: Oct. 18, 2006

(65) Prior Publication Data

US 2007/0065517 A1    Mar. 22, 2007

Related U.S. Application Data

(62) Division of application No. 10/616,776, filed on Jul. 10, 2003, now abandoned.

(60) Provisional application No. 60/395,537, filed on Jul. 12, 2002.

(51) Int. Cl.
*A61K 9/14* (2006.01)

(52) U.S. Cl.
USPC .......................................... 424/489; 514/618

(58) Field of Classification Search
None
See application file for complete search history.

(56) References Cited

U.S. PATENT DOCUMENTS

| | | | |
|---|---|---|---|
| 1,570,994 A | 1/1926 | Cook | |
| 4,002,718 A | 1/1977 | Gardella et al. | 424/37 |
| 4,122,157 A | 10/1978 | Huber | 424/21 |
| 4,177,290 A | 12/1979 | Lafon | 424/324 |
| 4,196,188 A | 4/1980 | Besins | 424/37 |
| 4,329,363 A | 5/1982 | Dorn et al. | 424/320 |
| 4,332,721 A | 6/1982 | Bernini | 260/239.57 |
| 4,517,179 A | 5/1985 | Raghunathan | 514/249 |
| 4,623,588 A | 11/1986 | Nuwayser et al. | |
| 4,713,246 A | 12/1987 | Begum et al. | 424/455 |
| 4,880,623 A | 11/1989 | Piergiorgio et al. | 424/465 |
| 4,895,726 A | 1/1990 | Curtet et al. | 424/456 |
| 4,927,855 A | 5/1990 | Lafon | 514/618 |
| 5,021,242 A | 6/1991 | Romer et al. | 424/436 |
| 5,180,745 A | 1/1993 | Lafon | 514/618 |
| 5,202,129 A | 4/1993 | Samejima et al. | 424/489 |
| 5,281,607 A | 1/1994 | Stone et al. | 514/280 |
| 5,391,576 A | 2/1995 | Lafon | 514/618 |
| 5,401,776 A | 3/1995 | Laurent | 514/618 |
| 5,612,379 A | 3/1997 | Laurent | 514/618 |
| 5,618,845 A * | 4/1997 | Grebow et al. | 514/618 |
| 5,719,168 A | 2/1998 | Laurent | 514/357 |
| 5,843,347 A | 12/1998 | Nguyen et al. | 264/9 |
| RE37,516 E | 1/2002 | Grebow et al. | |
| 6,346,548 B1 | 2/2002 | Miller et al. | 514/618 |
| 6,455,588 B1 | 9/2002 | Scammell et al. | 514/618 |
| 6,462,089 B1 | 10/2002 | Battaglia et al. | 514/618 |
| 6,488,164 B2 | 12/2002 | Miller et al. | 214/618 |
| 2003/0055075 A1 * | 3/2003 | Rubsamen | 514/282 |
| 2003/0137067 A1 * | 7/2003 | Cooper et al. | 264/5 |
| 2004/0105891 A1 | 6/2004 | Bentolila et al. | 424/489 |
| 2004/0167225 A1 | 8/2004 | Singh et al. | 514/618 |
| 2004/0167255 A1 | 8/2004 | Lee et al. | 524/100 |

FOREIGN PATENT DOCUMENTS

| | | |
|---|---|---|
| EP | 0 097 071 B1 | 8/1985 |
| EP | 0 233 106 B1 | 5/1989 |
| EP | 594 507 A1 | 4/1994 |
| EP | 0 462 004 B1 | 9/1995 |
| EP | 547 952 B1 | 9/1995 |
| FR | 2 385 693 | 10/1978 |
| IN | 723/Del/2002 * | 7/2002 |
| RU | 2171674 C2 | 8/2001 |
| WO | WO 94/21371 A1 | 9/1994 |
| WO | WO 95/00132 A1 | 1/1995 |
| WO | WO 95/01171 A1 | 1/1995 |
| WO | 96/11001 A1 | 4/1996 |
| WO | WO 00/37055 | 6/2000 |
| WO | 01/58439 A1 | 8/2001 |
| WO | WO 02/10125 A1 | 2/2002 |
| WO | WO 02/096401 A1 | 12/2002 |
| WO | WO 2004/004692 A1 | 1/2004 |

OTHER PUBLICATIONS

Becue T. et al., "Confirmation of the Structure of By-Products in the Synthesis of Modafinil by Liquid Chromatography-Mass Spectrometry," *J. of Chromatography*, 1991, 557, 489-494.

Carlson, R.F., et al., "Efficacy and safety of reformulated, micronized glyburide tablets in patients with non-insulin-dependent diabetes mellitus: a multicenter, double-blind randomized trial," *Clin Ther*, 1993, 15(5), 788-796.

Drabowicz J. et al., "A convenient procedure for the oxidation of sterically hindered sulfides to sulfoxides," *Synthesis*, 1990, 937-938.

Drouin J.E. et al., "Optimization of the Mobile Phase for the Liquid Chromatographic Separation of Modafinil Optical Isomers on a Chiral-AGP Column," *J. of Chromatography*, 1992, 605, 19-31.

*Drugs of the Future*; "Modafinil," 1990, 15(2), 130-132.

FDA/CDER guidance document "Dissolution Testing of Immediate Release Solid Oral Dosage Forms," 1997, 1-11, A-1-A-2.

FDA/CDER guidance document "Immediate Release Solid Dosage Forms: Scale-up and Post Approval Changes (SUPAC-IR): Chemistry, Manufacturing and Controls, In Vitro Dissolution Testing and In Vivo Bioequivalence Documentation," 1995, 1-26, A1.

Fuxe K. et al., "Evidence for a Protective Action of the Vigilance Promoting Drug Modafinil on the MPTP-Induced Degeneration of the Nigrostriatal Dopamine Neurons in the black mouse: an immunocytochemical and biochemical analysis," *Exp Brain Res*, 1992, 88, 117-130.

Haleblian J.K., "Characterization of Habits and Crystalline Modification of Solids and Their Pharmaceutical Application," *Journal of Pharmaceutical Sciences*, 1975, 64(8), 1269-1288.

Hargrove, J.T., et al., Absorption of oral progesterone is influenced by vehicle and particle size, *Am. J. Obstet. Gynecol.*, 1989, 948-951.

Hörter D., et al., "Influence of Physicochemical Properties on Dissolution of Drugs in The Gastrointestinal Tract," *Adv Drug Deliv Rev*, 2001, 46(1-3), 75-87.

Keese, R. et al. *Fundamentals of Preparative Organic Chemistry* 1982, Ellis Horwood Ltd., XP002310738 pp. 18-20.

(Continued)

*Primary Examiner* — Hasan Ahmed

(57) ABSTRACT

Pharmaceutical compositions comprising modafinil in the form of particles of defined size and methods for preparing same. The particle size of modafinil can have a significant effect on the potency and safety profile of the drug.

7 Claims, 3 Drawing Sheets

(56) References Cited

OTHER PUBLICATIONS

Kondo, N., et al., "Pharmacokinetics of a micronized, poorly water-soluble drug, HO-221, in experimental animals," *Biol Pharm Bull*, 1993, 16(8), 746-800.
Lauharanta, J., et al., "Pharmacokinetics of 8-methoxypsoralen in serum and suction blister fluid," *Arch Dermatol Res*, 1982, 273(1/2), 111-114.
Lyons T.J. et al., "Modafinil: The Unique Properties of a New Stimulant," *Aviation, Space & Environ Med*, 1991, 432-435.
McInnes, G.T., et al., "Effect of micronization on the bioavailability and pharmacologic activity of spironolactone," *J Clin Pharmacol*, 1982, 22(8), 410-417.
Milhaud C., et al., "Effects of Modafinil, An Alpha I Adrenergic Type Psychostimulant on the Sleep of Monkeys," *Psychopharmacology*, 1988, 96, Abstract No. 31.05.09.
Milhaud C.L. et al., "Presentation of d'un Nouveau Stimulant:Le CRL-40476," *AGARD Conf Proc.*, 1987, 415, 5-1-5-7.
Moachon G. et al., "Simultaneous Determination of Modafinil and its Acid Metabolite by High-Performance Liquid Chromatography in Human Plasma," *J of Chromatography* B, 1994, 654, 91-96.
Ravin, L.J., "Preformulation," *Remington's Pharmaceutical Sciences*, 16$^{th}$ Ed., 1980, Chapter 75, 1355-1368.
*Remington's Pharmaceutical Sciences*, 16$^{th}$ Ed., 1980, 305-306.
Ripple, E.G., "Powders," *Remington's Pharmaceutical Sciences*, 16Ed., 1980, *Chapter 88*, 1535-1545.
Roze C., et al.,"Drug CRL 40 028-Induced Inhibition of Pancreatic Secretion in Rats," *Arch Int Pharmacodyn*, 1983, 265, 119-127.
Shah V.P. et al., "In Vitro Dissolution Profile Comparison—Statistics and Analysis of the Similarity Factor, $f_2$," *Pharmaceutical Research*, 1998, 15(6), 889-896.
Sheperd, J., "The fibrates in clinical practice: focus on micronised fenofibrate," *Atherosclerosis*, 1994, 110(*Suppl*), S55-S63.
Stolk, L.M.L., et al., "Comparison of bioavailability and phototoxicity of two oral preparations of 5-methoxypsoralen," *British J. of Dermatology*, 1985, 112, 469-473.
Treffel, P., et al., "A new micronized 5-methoxypsoralen preparation," *Acta Derm Venerol*, 1992, 72, 65-67.
Wadke D.A., et al., "Preformulation testing," *Pharmaceutical Dosage Forms: Tablets*, 2$^{nd}$ Ed., 1989, 1-73.
Wilson et al., Textbook of Organic Medicinal and Pharmaceutical Chemistry, 6$^{th}$ Ed., *J.B. Lippincott Company*, 1971, 386-387.
Provigil® (modafinil)—FDA Approved Drafting Labeling, NDA 20-717, http://www.fda.gov/cder/foi/label/1998/207171bl.pcif, 1998, 1-28.
Duteil, et al., *European Journal of Pharmacology*, 1990, 180, 49-58.
Saletu, B. et al., *J. Clin. Pharm. Res.*, 1989, IX(3), 183-195.
Bastuji, et al., *Prog. Neuro-Psychopharmacol & Biol. Psychiat.*, 1988, 12, 695-700.

\* cited by examiner

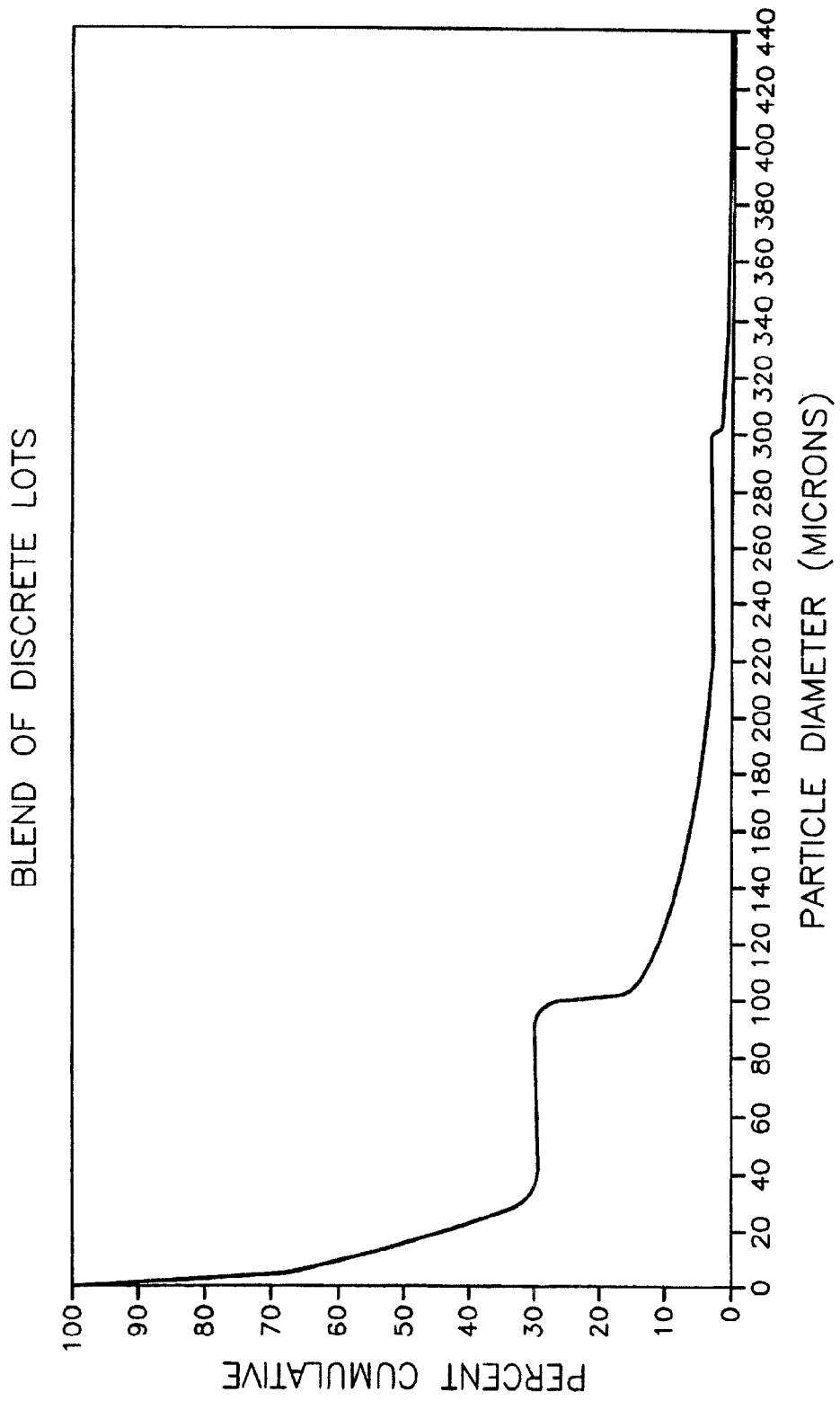

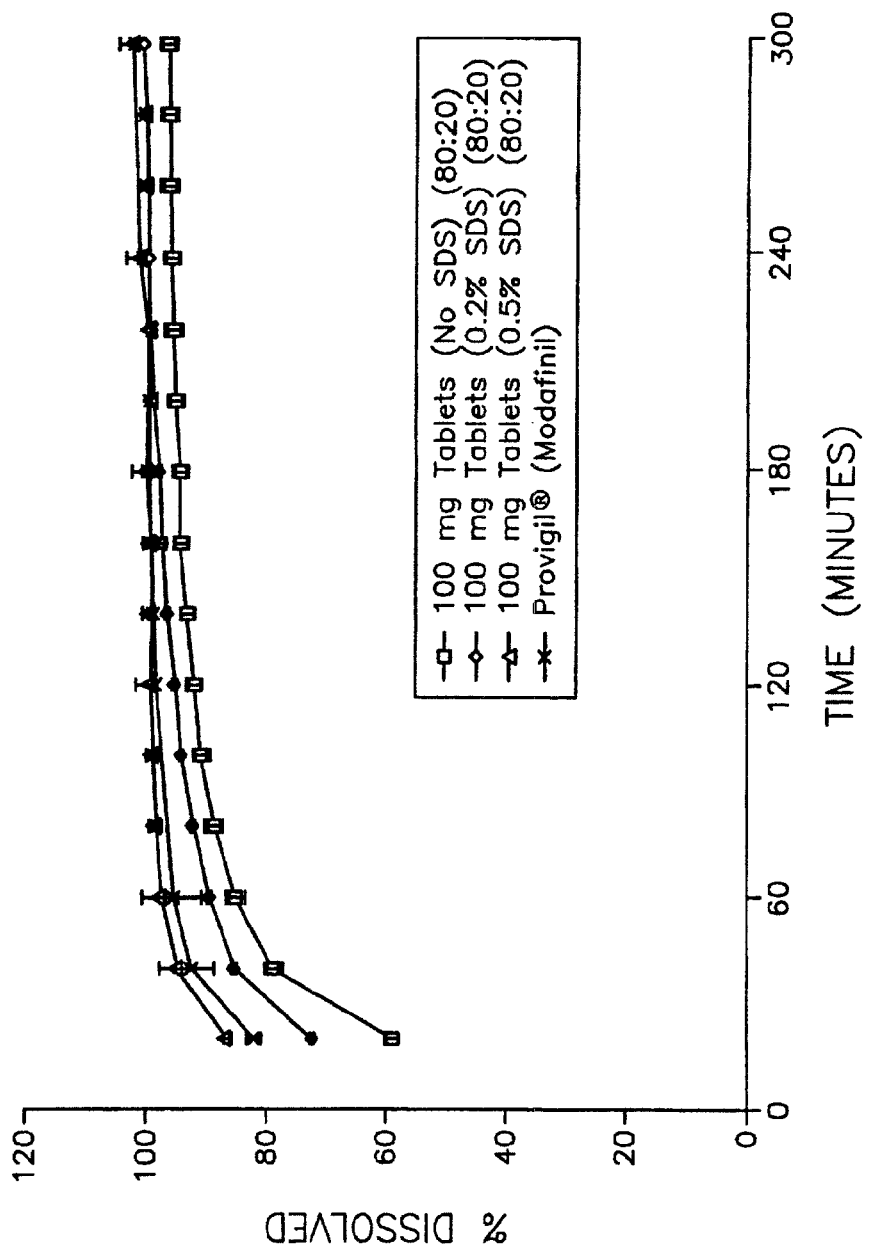
FIG. 3 EFFECT OF SDS ON DISSOLUTION PROFILE OF 100 mg TABLETS

MODAFINIL PHARMACEUTICAL COMPOSITIONS

CROSS-REFERENCE TO RELATED APPLICATIONS

This application is a divisional of copending U.S. application Ser. No. 10/616,776, filed Jul. 10, 2003, which in turn claims priority of U.S. Provisional Application No. 60/395,537, filed Jul. 12, 2002. The complete disclosure of each of these prior applications is hereby incorporated herein by reference in its entirety for all purposes.

FIELD OF THE INVENTION

This invention relates to the acetamide derivative modafinil. Modafinil ($C_{15}H_{15}NO_2S$), is 2-(benzhydrylsulfinyl)acetamide, and is also known as 2-[(diphenylmethyl)sulfinyl] acetamide.

BACKGROUND OF THE INVENTION

Modafinil has been described as presenting a "neuropsychopharmacological spectrum characterized by the presence of excitation with hyperactivity and of hypermotility; and by the absence of stereotypy (except in high doses) and of potentialisation of the effects of apomorphine and amphetamine" (U.S. Pat. No. 4,177,290; hereinafter "the '290 patent," which is incorporated herein by reference). A single administration of modafinil results in increased locomotor activity in mice and increased nocturnal activity in monkeys (Duteil et al., Eur. J. Pharmacol. 180:49 (1990)). The neuropsychopharmacological profile of modafinil has been distinguished from that of amphetamines (Saletu et al., Int. J. Clin. Pharm. Res. 9:183 (1989)). Modafinil is thought to modulate the central postsynaptic $alpha_1$-adrenergic receptor, without participation of the dopaminergic system (Duteil et al., supra). Modafinil has been successfully tested in humans for treatment of idiopathic hypersomnia and narcolepsy (Bastuji et al., Prog. Neuro-Psych. Biol. Psych. 12:695 (1988)).

Narcolepsy is a chronic disorder characterized by intermittent sleep attacks, persistent, excessive daytime sleepiness and abnormal rapid eye movement ("REM") sleep manifestations, such as sleep-onset REM periods, cataplexy, sleep paralysis and hypnagogic hallucinations, or both (Assoc. of Sleep Disorders Centers, Sleep 2:1 (1979)). Most patients with narcolepsy also have disrupted nocturnal sleep (Montplaisir, in Guilleminault et al. eds., Narcolepsy, Spectrum Pub., New York, pp. 43-56). Pathological somnolence, whether due to narcolepsy or other causes, is disabling and potentially dangerous. Causes of pathological somnolence, other than narcolepsy, include chronic sleep loss (Carskadon et al., Sleep, 5:S73 (1982); Carskadon et al., Psychophysiology, 18:107 (1981)); sleep apnea (Kryger et al., Principles and Practice of Sleep Medicine, W. B. Saunders Co., Philadelphia, Pa. (1989)); and other sleep disorders (International Classification of Sleep Disorders: Diagnostic and Coding Manual, American Sleep Disorder Association, Rochester, Minn. (1990)). Whether due to narcolepsy or other causes, pathological somnolence produces episodes of unintended sleep, reduced attention, and performance errors. Consequently, it is linked to a variety of transportation and industrial accidents (Mitler et al., Sleep 11:100 (1988)). A therapeutic agent that reduces or eliminates pathological somnolence would have important implications not only for individual patients, but also for public health and safety.

Other uses of modafinil have been presented. U.S. Pat. No. 5,180,745 discloses the use of modafinil for providing a neuroprotective effect in humans, and in particular for the treatment of Parkinson's disease. The levorotatory form of modafinil, i.e., (−) benzhydrylsulfinyl-acetamide, may have potential benefit for treatment of depression, hypersomnia and Alzheimer's disease (U.S. Pat. No. 4,927,855). European Published Application 547952 (published Jun. 23, 1993) discloses the use of modafinil as an anti-ischemic agent. European Published Application 594507 (published Apr. 27, 1994) discloses the use of modafinil to treat urinary incontinence.

U.S. Pat. No. RE37,516 discloses pharmaceutical compositions having a defined particle size, and in particular compositions wherein 95% of the cumulative total of the effective amount of modafinil particles in the composition have a diameter less than about 200 microns.

SUMMARY OF THE INVENTION

The present invention discloses a composition including, but not limited to, a pharmaceutical composition, of modafinil in the form of a particle blend of "small particles," "large particles" and optionally "very large particles." By properly controlling the distribution and quantity of small particles, large particles, and very large particles in the blend, dissolution and absorption post-ingestion of the pharmaceutical composition can be optimized, thereby providing a composition that is effective to alter the somnolent state of a subject.

In one embodiment, the present invention includes a pharmaceutical composition having two or more portions of solid modafinil particles from a bulk batch of modafinil. Each portion of modafinil has a bounded particle size range and one or more particle size ranges present in the bulk batch are not represented in the pharmaceutical composition.

In another embodiment, the present invention includes a pharmaceutical composition also having two or more portions of solid modafinil particles. However, each portion has a bounded particle size range and there is a particle size range between the size ranges represented in the two or more portions that is not represented in the pharmaceutical composition.

In one embodiment, the present invention is a pharmaceutical dosage form including an amount of modafinil effective to alter the somnolent state of a mammal upon oral administration. The dosage form is made from a pharmaceutical composition of the present invention which includes at least a first portion and a second portion of modafinil being in the form of solid modafinil particles and each having a bounded particle size distribution. The second portion can be from the same bulk batch as the first portion or from a different bulk batch. When combined, the first portion and the second portion yield a mixture having a bounded particle size distribution that is different than the particle size distribution of the bulk batches.

The pharmaceutical composition can also include a second portion of modafinil being in the form of solid modafinil particles having a particle size distribution different than the particle size distribution of the first portion.

In another embodiment, the method of formulating a pharmaceutical composition of modafinil includes the steps of providing a batch of modafinil, wherein the particles in the batch have a distribution of particle diameters. The next step is separating the particles in the batch of modafinil into at least two discrete lots of modafinil particles, wherein each discrete lot contains modafinil of a bounded range of particle diameters, thereby forming at least a first discrete lot and a second discrete lot. Then, a next step is blending a portion of the first lot with all or a portion of the second lot and then forming a pharmaceutical composition of modafinil from the blend of the first lot and the second lot portions.

In another embodiment, the present invention includes a pharmaceutical dosage unit comprising an effective amount of modafinil wherein at least about 10% of the total cumulative modafinil particles are smaller than about 25 microns in diameter and more than about 5% of the total cumulative particles are greater than 220 microns in diameter.

In yet another embodiment, the present invention includes a method of formulating a pharmaceutical composition of modafinil including the steps of providing a first batch and a second batch of modafinil, wherein the particles in each batch have a distribution of particle diameters, separating the particles of the first batch of modafinil into at least two discrete lots of modafinil particles, wherein each discrete lot contains modafinil of a defined particle diameter, thereby forming at least a first discrete lot and a second discrete lot, recombining at least one of the discrete lots with the second batch, and then altering the distribution of particle diameters of the particles in the second batch.

In yet another embodiment, the present invention includes a method of altering the somnolent state of a mammal, such as a human, by administering to the mammal an effective amount of the composition of the present invention.

BRIEF DESCRIPTION OF THE DRAWINGS

FIG. 2 is a graph depicting a particle size distribution of a blended modafinil composition that can be prepared in accordance with the present invention.

FIG. 3 is a graph depicting dissolution profiles for four tablets that can be made in accordance with the present invention.

DETAILED DESCRIPTION

Figure 1:
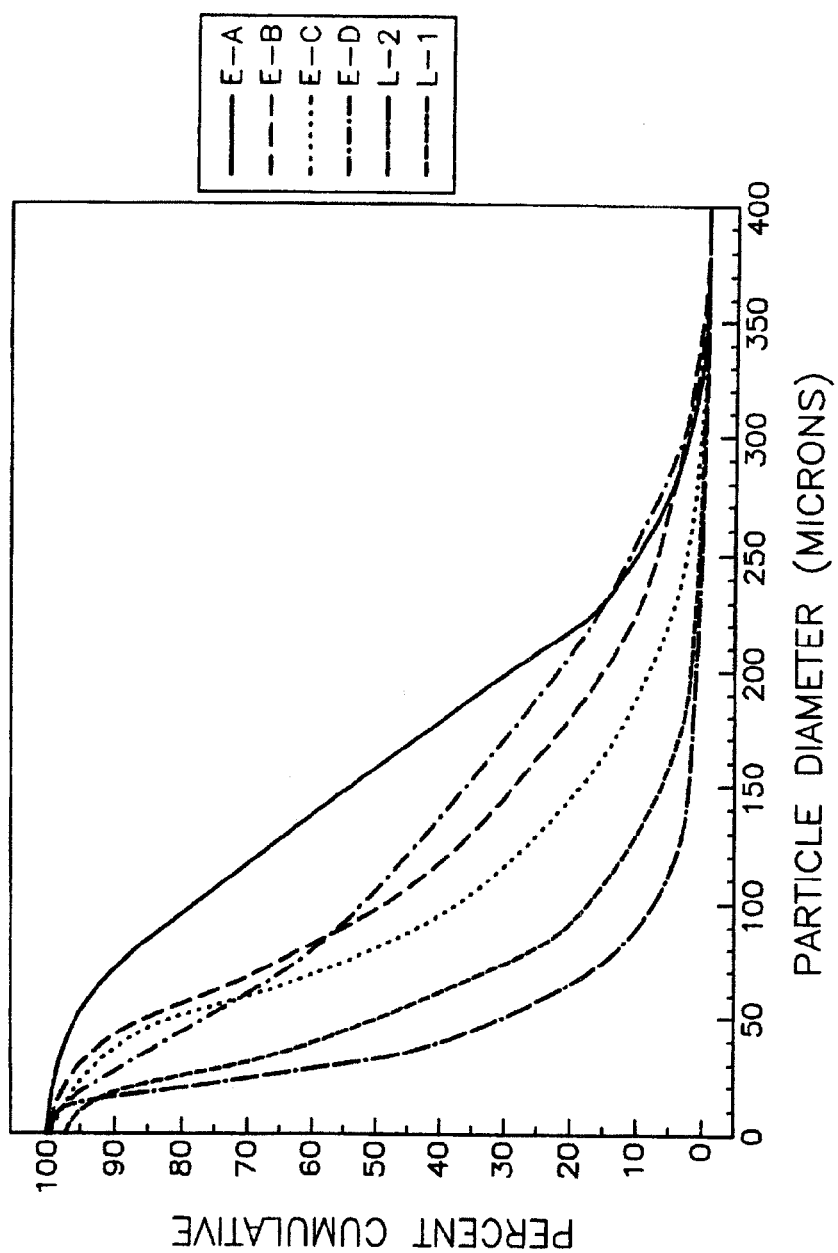
FIG. 1 is a graph depicting particle size distributions for six batches of modafinil.

The present invention results from the discovery that the particle size distribution of modafinil, and the consistency of the particle sizes that make up the distribution, affects the effective dissolution and absorption of modafinil from a dosage form containing the modafinil particles. Specifically, by customizing and controlling the particle size distribution of a blend of small, large and optionally very large particles of modafinil, the dissolution and absorption properties of a dosage form of modafinil, post-ingestion, can be optimized. The optimized modafinil provides drug products which 1) can have substantially similar dissolution profiles to currently marketed and FDA approved modafinil products, and 2) can be bioequivalent to currently marketed and FDA approved modafinil products. Drug product comparative study techniques designed to show whether drug products exhibit substantially similar profiles are described in the FDA/CDER guidance document "Dissolution Testing of Immediate Release Solid Oral Dosage Forms (August 1997)," which is hereby incorporated by reference. Other suitable references also can include "In Vitro Dissolution Profile Comparison— Statistics and Analysis of the Similarity Factor, f2" by V. P. Shah et al. in Volume 15, No. 6, pages 889-896 of Pharmaceutical Research (1998), as well as another FDA/CDER guidance document entitled "Immediate Release Solid Dosage Forms: Scale-up and Post Approval Changes (SUPAC-IR): Chemistry, Manufacturing and Controls, In Vitro Dissolution Testing and In Vivo Bioequivalence Documentation (November 1995)," the contents of which are hereby incorporated by reference. Bulk batches of modafinil, which are typically used to make dosage forms containing modafinil, such as Provigil® (modafinil), can be manufactured in accordance with methods understood by one of ordinary skill in the art, including those described in the '290 Patent. These bulk batches of modafinil can contain particles having a distribution of particle diameters from smaller than 10 microns to larger than 1500 microns. FIG. 1 shows the particle size distribution for six bulk batches of modafinil which can be used to make the composition of the present invention. As further shown in FIG. 1, each of the six bulk batches contains small, large and in some cases very large particles, and each bulk batch has a different particle size distribution curve relative to the other five bulk batches. It follows that dosage forms made from these bulk batches typically exhibit similar particle size distribution curves to the bulk batch from which the dosage forms originated. Of the six bulk batches, L-2 and L-1 are closest to the particle size distribution of currently marketed and FDA approved modafinil products, such as Provigil® (modafinil). As disclosed herein and as used in the compositions and methods of the present invention, a modafinil compound can include a racemic mixture, and can optionally be in an acid form, such as a metabolic acid of modafinil or a benzhydrylsulfinylacetic acid, a sulfone form, a hydroxylated form, a conjugated form such as a modafinil compound conjugated to a protein, a polysaccharide, a glucuronide or a sulfate, or a polymorphic form, it may include compounds containing isosteric replacements of the phenyl groups of modafinil, and polymorphic species or analogs of modafinil, or derivatives of cogeners and prodrugs. In preferred embodiments, the modafinil compound is modafinil. Prodrugs are known in the art as compounds that are converted to the active agent (modafinil) in the body of a subject.

As described above, an aspect of the present invention involves the discovery that the consistency of the particle sizes that make up a particle distribution of modafinil can affect the dissolution and absorption of a dosage form containing modafinil. Accordingly, the present invention is directed to a more consistent particle size distribution of particles in a pharmaceutical composition and/or dosage forms containing modafinil. To this end, the particles in a bulk batch can be separated into discrete lots having a more narrowly defined and/or consistent particle size distribution as compared to the bulk batch.

Discrete Particle Size Lots Modafinil

To achieve a more consistent particle size distribution of particles of modafinil for use in making a pharmaceutical composition and/or dosage form of the present invention, particles of the bulk batch can be passed through a series of separation screens or filters. Each separation screen has openings from about 500 microns or more in diameter to about 10 microns or less in diameter. It is preferred that each separation screen has openings with consistently sized openings such that substantially all of the openings of the screen are the same size.

The particles can be first passed through a separation screen having the largest openings. The size of the openings of subsequent separation screens can be incrementally reduced by 5 microns, 10 microns, 20 microns, or 50 microns in diameter. However, it will be apparent to one of skill in the art that the diameter of the openings in a separation screen can be reduced (relative to a preceding separation screen) by any appropriate amount to meet the particular needs of the artisan.

Further, in another embodiment, it is recognized that the particles can first be passed through a separation screen having the smallest openings to sift out the smaller diameter particles and retain larger particles. The larger particles can then be transferred to a second screen (or additional screens) with slightly larger openings than the preceding screen to sift out larger particles. Typically, the openings of subsequent separation screens are typically incrementally increased by 5 microns, 10 microns, 20 microns, or 50 microns in diameter. Although separating the bulk modafinil into discrete lots using incrementally larger openings is practicable and within the ability of one skilled in the art in light of the teachings herein, the remainder of this disclosure refers to particles sequentially separated into discrete lots using screens with incrementally reduced sized openings.

Thus, the particles retained on a separation screen have diameters which are larger or equal to the diameters of the separation screen's openings, but smaller in diameter than the preceding separation screen's openings.

The particles of modafinil that are retained by each separation screen are then deposited into an acceptable container to form discretely sized particle lots (hereafter "discrete lots") having a bounded particle diameter range. The formation of discrete lots is further detailed in Example 1. The containers preferably have a label indicating the diameter of the modafinil particles in the container as defined by the diameters of the retaining and preceding screens' openings, thereby setting the contained particles' diameter boundaries. For example, one container may indicate modafinil particles having a diameter of "smaller than or equal to 200 microns, larger than or equal to 180 microns" or "$180 \leq P \leq 200$," as detailed further below. The total number of particles and the diameter of each of the particles in the discrete lot can also be measured using techniques known in the art to provide more detailed statistical information such as, but not limited to, mean particle size and standard deviations from the mean particle size. The discrete lot can also be assigned a "predicted mean particle diameter," which is the mean of the two separation screens used to separate the modafinil of the discrete lot. Accordingly a container indicating particles having a diameter of "smaller than 200 microns, larger than or equal to 180 microns" would have a predicted mean particle diameter of 190 microns. The predicted mean particle diameter may or may not be equal to the actual mean particle diameter of the discrete lot.

Furthermore, in this manner multiple bulk batches can be easily processed together and simultaneously separated into discrete lots. The discrete lots, each containing particles of modafinil within a bounded range of particle diameters, can then be used in the manner described herein, thereby reducing the difficulties associated with particle size inconsistencies between bulk batches in the formation of pharmaceutical compositions and dosage forms.

The discrete lots can be separated into small particle discrete lots, large particle discrete lots, and very large particle discrete lots. Typical small particle discrete lots can include particles (P) in about the following bounded ranges (values of "P" are particle diameters in microns): $0.01 \leq P \leq 200$, $0.01 \leq P \leq 40$, $40 \leq P \leq 80$, $80 \leq P \leq 120$, $120 \leq P \leq 160$, $160 \leq P \leq 200$, $0.01 \leq P \leq 10$, $10 \leq P \leq 20$, $20 \leq P \leq 30$, $30 \leq P \leq 40$, $40 \leq P \leq 50$, $50 \leq P \leq 60$, $60 \leq P \leq 70$, $70 \leq P \leq 80$, $80 \leq P \leq 90$, $90 \leq P \leq 100$, $100 \leq P \leq 110$, $110 \leq P \leq 120$, $120 \leq P \leq 130$, $130 \leq P \leq 140$, $140 \leq P \leq 150$, $150 \leq P \leq 160$, $160 \leq P \leq 170$, $170 \leq P \leq 180$, $180 \leq P \leq 190$, $190 \leq P \leq 200$ and combinations thereof.

Typical large particle ranges include particles (P) in the following bounded ranges (in microns): $220 < P \leq 400$, $220 < P \leq 310$, $310 \leq P \leq 400$, $220 < P \leq 230$, $230 \leq P \leq 240$, and $240 \leq P \leq 250$. The bounded range further includes about: $250 \leq P \leq 260$, $260 \leq P \leq 270$, $270 \leq P \leq 280$, $280 \leq P \leq 290$, $290 \leq P \leq 300$, $300 \leq P \leq 310$, $310 \leq P \leq 320$, $330 \leq P \leq 340$, $340 \leq P \leq 350$, $350 \leq P \leq 360$, $360 \leq P \leq 370$, $370 \leq P \leq 380$, $380 \leq P \leq 390$, $390 \leq P \leq 400$ and combinations thereof.

Typical very large particle ranges include particles (P) in the following bounded ranges (in microns): $400 \leq P \leq 410$, $410 \leq P \leq 420$, $420 \leq P \leq 430$, $430 \leq P \leq 440$, $440 \leq P \leq 450$, $450 \leq P \leq 460$, $460 \leq P \leq 470$, $470 \leq P \leq 480$, $480 \leq P \leq 490$, and $490 \leq P \leq 500$ and combinations thereof.

In some instances, particles of modafinil can be retained on a separation screen wherein a portion of the retained particles are smaller than the separation screen's openings. Thus, a discrete lot may contain a portion of particles of modafinil having smaller diameters than the particles' diameters which have been defined by the separation screen. This retention can be the result of many factors such as static charge on the modafinil particles. Typically, less than about 15% of the cumulative total of all modafinil particles retained on a separation screen have diameters smaller than the diameters of the separation screen's openings. Preferably, less than about 5% and most preferably less than about 2% of the cumulative total of all modafinil particles retained on a separation screen have diameters smaller than the diameters of the separation screen's openings.

Similarly, because of the irregular shape of modafinil particles, and in particular because the particles are not truly spherical, in some instances particles of modafinil can be retained on a separation screen which are larger in theoretical diameter than the preceding separation screen's openings. Essentially, larger particles of modafinil pass through a screen having opening diameters which are smaller than the theoretical diameter of the modafinil particles. Accordingly, the next separation screen may retain particles that have diameters which are larger than the preceding separation screen. Typically, less than about 15% of the cumulative total of all modafinil particles retained on a separation screen have diameters larger than the diameters of the preceding separation screen's openings. Preferably, less than about 5% and most preferably less than about 2% of the cumulative total of all modafinil particles retained on a separation screen have diameters larger than the diameters of the preceding separation screen's openings.

In some embodiments, it is preferred that the particles of modafinil in each discrete lot have diameters which are as consistent as practicable with the other particles in the discrete lot. To this end, the discrete lots can be repeatedly subdivided, filtered, and/or screened in the manner described above.

Other methods, such as milling, micronization, separation by weight, separation by density, etc., can also be employed to form lots of pre-determined or bounded particle sizes. The particles can then be placed in the appropriate discrete lot container. Alternatively, small, large and very large particles can be compacted into larger particles. The compacted particles can then be placed in the appropriate discrete lot container.

Blends of Discrete Lots

After the modafinil particles have been separated by particle diameter into discrete lots, the contents of one or more of the discrete lots can be used to create pharmaceutical compositions of the present invention. In one embodiment, at least two discrete lots can be combined to create a pharmaceutical composition of the present invention. The modafinil from the discrete lots can be combined together either by weight or by number of particles, as described in more detail below.

In accordance with the present invention, the optimal ratio (by weight or by cumulative total of particles) of small to large (and optionally very large) modafinil particles in a blend of the present invention further depends upon the size of the particles used in the final pharmaceutical composition. By appropriately blending small, large, and optionally very large particles, the dissolution profile of the blended lot can be made to simulate the dissolution profile of the modafinil composition in which greater than or equal to 95% of the particles in the effective amount are small particles, i.e., less than about 200 microns. For example, if a greater amount of particles having a mean/average diameter smaller than about 100 microns are employed in a pharmaceutical composition, then the diameter of the modafinil particles which make up the balance of the pharmaceutical composition can be larger than if the small particles are, e.g., smaller than or equal to about 200 microns in diameter, were used.

In one embodiment of the present invention, particles of modafinil from at least one discrete lot are processed to provide a pharmaceutical composition and dosage forms having a similar dissolution profile to PROVIGIL® (modafinil), 100 milligram (mg) or 200 milligram pharmaceutical compositions, and in particular pharmaceutical compositions that release at least 80% of the modafinil in 45 minutes in a 0.1 N HCl solution.

The present invention also extends to formulations which are bioequivalent to available formulations of modafinil, in terms of both rate and extent of absorption, for instance as defined by the US Food and Drug Administration and discussed in the so-called "Orange Book" (Approved Drug Products with Therapeutic Equivalence Evaluations, US Dept of Health and Human Services, 22nd edn., 2002), the content of which is hereby incorporated by reference. In one embodiment, particles of modafinil from at least one discrete lot are processed to provide a pharmaceutical composition having bioequivalence to PROVIGIL® (modafinil), 100 milligram or 200 milligram pharmaceutical compositions. Preferably, an embodiment of the present invention contains particles of modafinil which are blended in such a manner to have the same dissolution profile and be bioequivalent to PROVIGIL® (modafinil), 100 milligram or 200 milligram pharmaceutical compositions.

In another embodiment, the present invention includes a pharmaceutical composition of modafinil, or a dosage form including modafinil having an amount of modafinil effective to alter the somnolent state of a mammal upon oral administration. The effective amount of modafinil includes modafinil from at least one discrete lot from a bulk batch, and typically at least two discrete lots. In certain embodiments, the components include:

a) a first portion of modafinil being in the form of solid modafinil particles from a bulk batch having a bounded particle size distribution, an average particle size (which may or may not equal the predicted mean particle diameter); and b) an optional second portion of modafinil being in the form of solid modafinil particles, which may or may not be from the same bulk batch as the first portion, having a bounded particle size distribution.

In one embodiment, the combination of the first portion and the second portion yields a bounded particle size distribution that is different than the particle size distribution of the bulk batch and the other bulk batch if the second portion comes from a bulk batch which is different from the bulk batch of the first portion.

In one embodiment, the pharmaceutical composition includes two or more portions of solid modafinil particles from a bulk batch of modafinil. In the composition, each portion has a bounded particle size range and one or more particle size ranges present in the bulk batch are not represented in the pharmaceutical composition.

In another embodiment, the pharmaceutical composition includes two or more portions of solid modafinil particles. In this particular embodiment, each portion has a bounded particle size range and there is a particle size range between the size ranges represented in the two or more portions that is not represented in the pharmaceutical composition.

In one embodiment of the invention, more than about 5% of the particles in the composition are larger than about 200 microns in diameter. In another embodiment, the composition has approximately the same dissolution profile as a modafinil composition in which at least about 95% of the particles in an effective amount of modafinil are smaller than about 200 microns in diameter. In yet another embodiment, the composition has approximately the same dissolution profile as PROVIGIL® (modafinil), and preferably at least 80% of the modafinil dissolves after 45 minutes in a 0.1N solution of HCl.

In another embodiment, a composition of the present invention is bioequivalent to a modafinil composition wherein at least about 95% of the particles in an effective amount of modafinil are smaller than about 200 micronsin diameter, and is preferably the composition of the present invention is bioequivalent to PROVIGIL® (modafinil).

In some embodiments of the blend of the present invention, fewer than about 85% of the particles can be small particles, i.e., smaller than about 200 microns in diameter. In other embodiments, fewer than about 75% of the particles can be small particles. In still other embodiments, fewer than about 65% of the particles can be small particles. In yet other embodiments, fewer than about 50% of the particles can be small particles.

In some embodiments, the small particles can be smaller than about 175 microns, typically smaller than about 150 microns, and more typically smaller than about 125 microns in diameter. In other embodiments, the small particles can be smaller than about 100 microns, typically smaller than 75 microns in diameter. In yet other embodiments, the small particles can be smaller than about 50 microns, typically smaller than about 25 microns and can be as small as about 10 microns or 0.01 microns or less in diameter.

A pharmaceutical composition of the present invention can include modafinil prepared by the process of blending a first and a second portion of solid modafinil particles wherein the first portion has a pre-determined particle size range and the second portion has a pre-determined particle size range that is different from that of the first portion.

Additional portions of modafinil being in the form of solid modafinil particles can also be used and added to the first and second portions. Each additional portion also has a bounded particle size distribution and selected from a discrete lot which is different from the discrete lots used for the first and/or second portion. When combined, the composition can provide a particle size distribution that is different from the particle size distribution of one or more bulk batches In yet another pharmaceutical composition or dosage form of the present invention, the composition or dosage form includes an amount of modafinil effective to alter the somnolent state of a mammal upon oral administration and is manufactured by preparing a bulk batch and removing from the bulk batch at least one discrete lot of particles having a bounded particle size range.

In addition to making pharmaceutical compositions of modafinil from discrete portions, as described above, modafinil being in the form of solid modafinil particles having a particle size distribution and selected from one or more discrete lots can be combined with modafinil from a bulk batch to adjust the particle size distribution of the bulk batch. In particular, one or more discrete lots can be added to a bulk batch of modafinil having a particle size distribution, thereby enhancing the particle size distribution of the bulk batch.

Alternatively, modafinil from a bulk batch can be processed in accordance with the techniques described above to remove particles of a certain diameter from the batch. Specifically, the bulk batch is first separated into discrete lots, and the lots containing undesired particles are removed. The remaining discrete lots can be recombined to form a blend having a particle size distribution which is different from the particle size distribution of the original bulk batch.

In some embodiments, particles can be removed from the bulk batch in the manner described above and then a portion from a discrete lot containing additional particles having a different bounded diameter range than those particles which were removed can be added to the batch. In this manner, in some embodiments pharmaceutical compositions of the present invention contain particles which are not present in the same proportion that existed in a bulk batch.

Once combined, analysis of the particles within the pharmaceutical composition of the present invention can generate a cumulative particle size distribution curve, such as the curve depicted in FIG. 2 (described in more detail below). It is because of the mechanical separation and recombination of particles, that pharmaceutical compositions of the current invention can exhibit particle size distribution curves that are not attainable via normal chemical synthesis routes. This is exemplified by a comparison of the curves set forth in FIG. 1 and FIG. 2. Further, a pharmaceutical composition of the present invention can exhibit a particle size distribution curve that is different from at least one, and preferably all of the particle size distribution curves attributable to any one or more (if more than one bulk batch is used) of the bulk batches used to create the discrete lots.

Excipients and Other Ingredients

Although the compositions and methods disclosed herein have been described in light of certain preferred embodiments, it is understood that the modafinil compounds described herein may be orally administered with an inert diluent or an assimilable edible carrier, for example. The compositions may also be enclosed in a hard or soft shell gelatin capsule, compressed into tablets, or incorporated directly with food of the diet. For oral therapeutic administration, the active compounds such as modafinil may be incorporated with excipients and used in the form of ingestible tablets, buccal tablets, troches, capsules, elixers, suspensions, syrups, wafers, and the like, although tablets are the generally preferred method of administering modafinil. Such compositions and preparations should contain at least 0.1% of active compound. The percentage of the compositions and preparations may, of course, be varied and may conveniently be between about 2 and about 60% of the weight of the unit.

The tablets, troches, pills, capsules, powders, liquid/suspensions or emulsions and the like may also contain any of the following: a binder, such as gum tragacanth, acacia, corn starch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring, for example. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixer may contain the active compounds sucrose as a sweetening agent and methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparations and formulations.

In certain embodiments, the disclosed compositions may be formulated to be administered by use of a skin patch, or transdermal delivery system. The transdermal administration of the modafinil compositions described herein may be accomplished by any number of systems known in the art.

These methods typically include an adhesive matrix or drug reservoir system and may include a skin permeation enhancement agent such as ethanol, polyethylene glycol 200 dilaurate, isopropyl myristate, glycerol trioleate, linolenic acid saturated ethanol, glycerol monooleate, glycerol monolaurate, n-decyl alcohol, capric acid, and certain saturated and unsaturated fatty acids, and their esters, alcohols, monoglycerides, acetates, diethanolamides and N,N-dimethylamides.

Iterative Test of the Pharmaceutical Composition

As described above, the optimal ratio of small to large (and optionally very large) modafinil particles in a blend of the present invention depends upon the size of the particles used in the final pharmaceutical composition. A pharmaceutical composition of the present invention, once processed into a dosage form (such as a tablet), can exhibit a similar dissolution profile to Provigil® (modafinil), and preferably a dosage form of the present invention is bioequivalent to Provigil® (modafinil), the commercial form of modafinil. However, one of skill in the art understands that not all combinations of small, large and very large particles in the pharmaceutical composition will exhibit one or both of these desirable characteristics. Accordingly, it is to be expected that routine experimentation will be desirable to determine the optimum particle size makeup and proportions of blend mixtures that exhibit similar dissolution profiles and/or are bioequivalent to Provigil® (modafinil).

In some embodiments, disintegrants are added to the formulation to help the tablet disintegrate after consumption, thereby releasing the active ingredients. Some common disintegrants include several modified cellulose derivatives, such as crosscarmellose sodium and other modified starch derivatives such as sodium starch glycolate. It will also be understood by one of ordinary skill in the art that other ingredients, binders and lubricants can further affect the dissolution profile of the dosage form.

Further, surfactants, such as ionic, non-ionic and/or bile salt surfactants, can also be included in the present invention. Anionic surfactants include, but are not limited to, sodium alkyl sulfate (Sodium Lauryl Sulphate®) as well as sulfosuccinate derivatives such as docusate sodium. Non-ionic surfactants include, but are not limited to, polyoxyethylene sorbitan fatty acid esters (polysorbates) such as Tween 20®, Tween 80®, Tween 40®, Span 20®, fatty acid esters of polyethylene glycols such as Gelucire 44/14®, Gelucire 50/13 ®, saturated polyglycolized (including mono, di or tri) glycerides, medium chain monoglycerides (from 6 to 10 carbon atoms long) such as glyceryl monocaprylate (Imwitor 308®), glyceryl monocaproate (Capmul MCM C-8®), glyceryl caprylate/caprate (Capmul MCM®), polyoxyethylene glyceryl caprylate and polyoxyethylene glyceryl caproate (Labrasol®), medium chain fatty acid esters such as glyceryl tri caprate and glyceryltricarilate (Miglyol 612®), block polymers of ethylene oxide and propylene oxide, polyoxyethylene-polyoxy propylene block copolymers such as Poloxamer 188 (Pluronic F-68®), Poloxamer 237 (Pluronic F-87®), Poloxamer 338 (Pluronic F-108®), Poloxamer 407 (Pluronic F-127®), Poloxamer 124 (Pluronic L-44®), polyoxyl stearate-polyethoxylated (40) stearic acid (Myrj 52®), ethoxylated castor oil-polyethoxylated (60) hydrogenated castor oil (Cremophor EL®), ethoxylated hydrostearic acidpolyethylene glycol 660 hydroxystearate (Solutol® HS 15), polyoxyethylene alkyl ethers (from 12 to 18 carbon atoms long) such as polyoxyl 20 cetostearyl ether (Atlas G-3713®), polyoxyl 10 oleyl ether (Brij 96®, Brij 97®, Oleth 10®), polyethylene glycol ether (Triton X-100®, Triton X-114®, Triton X-405®, Triton N-101®) and lecithins such as phospholipids (dimyristoyl DL-alpha-phophatidylcholine). Bile salt surfactants include, but are not limited to deoxycholic acid, sodium deoxycholate, cholic acid, sodium taurocholate.

Formulation and Administration

An appropriate dosage for modafinil having a defined particle size is between about 10 milligram and about 800 milligram of modafinil, more typically between about 15 milligrams and 800 milligrams of modafinil.

The pharmaceutical composition described herein is most preferably administered orally in the form of a vehicle such as a tablet, capsule, powder, pill, liquid/suspension or emulsion. The administration vehicle may comprise a pharmaceutically-acceptable carrier. The carrier may comprise agents that aid solubility, absorption, flavor, color or texture of the vehicle or its contents. Topical administration via an epidermal patch or the like, or administration via direct injection of the drug, is also acceptable.

A vehicle of the invention can include + or −10-15% of the modafinil particles, due to factors such as vehicle manufacturing tolerances and expected shelf life of the modafinil. For example, a vehicle labeled as containing 50 milligrams can be initially prepared with, e.g., 55 or 58 milligrams of modafinil, with the expectation that after one month to two years of storage, the active amount of modafinil therein has decreased. Vehicles prepared with such adjustments in order to compensate for the expected degradation of the drug fall within the scope of the invention.

Specific Illustrative Embodiments of Pharmaceutical Compositions and Dosage Units In order to develop modafinil based products that have similar dissolution profiles and/or bioequivalence to FDA approved modafinil products such as Provigil® (modafinil), and/or which include at least the least amount of modafinil effective for treating a somnolent or somnolescent state, it is desirable to tailor the blends of modafinil. In one embodiment, all of the portions of modafinil are taken from discrete lots having mean particle diameters smaller than or equal to about 200 microns (small particles). In another embodiment, at least 95% of the cumulative total of modafinil particles in the entire pharmaceutical composition are small particles having diameters smaller than or equal to about 200 microns. In yet another embodiment, the pharmaceutical composition contains at least 15 milligrams of modafinil taken from a discrete lot having an average particle size smaller than or equal to about 10 microns to about 80 microns in diameter, with the remainder of the pharmaceutical composition (by weight) including additional small particles and/or large and/or very large particles of modafinil.

In another embodiment, at least 25% to 100% of the cumulative total of particles of a first portion have diameters smaller than or equal to about 20 microns. In still another embodiment, the first portion contains modafinil in the form of solid particles, wherein at least 50% to 100% of the particles of the first portion have diameters smaller than or equal to about 30 microns. In another embodiment, the first portion contains modafinil in the form of solid particles, wherein at least 70% to 100% of the particles of the first portion have diameters smaller than or equal to about 40 microns. In other embodiments, the first portion contains modafinil in the form of solid particles, wherein at least 75% to 100% of the particles of the first portion have diameters smaller than or equal to about 50 microns. In yet another embodiment, the first portion contains modafinil in the form of solid particles, wherein at least 80% to 100% of the particles of the first portion have diameters smaller than or equal to about 60 microns. In still another embodiment, the first portion contains modafinil in the form of solid particles, wherein at least 85% to 100% of the particles of the first portion have diameters smaller than or equal to about 70 microns. In another embodiment, the first portion contains modafinil in the form of solid particles, wherein at least 90% to 100% of the particles of the first portion have diameters smaller than or equal to about 80 microns.

As described above, the second and/or additional portions can contain small particles. However, the second or additional portions can also contain large particles of modafinil, and in particular particles having diameters larger than 220 microns and smaller than or equal to 440 microns. In other embodiments, the second portion contains modafinil particles having diameters larger than 220 microns and smaller than about 350 microns. In still other embodiments, the second portion contains modafinil particles having diameters larger than 220 microns and smaller than about 300 microns. In yet another embodiment, the second portion contains modafinil particles having diameters larger than 220 microns and smaller than about 250 microns. Further, in some embodiments, preferably no more than 50% and more preferably no more than 20% of the cumulative total of modafinil particles can be very large particles (particles having a diameter larger than 440 microns).

In one embodiment of a pharmaceutical composition of the present invention, the first portion of small particles includes less than 90% of the cumulative total of modafinil particles in the pharmaceutical composition. In another embodiment of a pharmaceutical composition of the present invention, the second portion (and any further portions) of large or very large particles includes greater than 10% of the cumulative total of modafinil particles in the pharmaceutical composition, such that the first and second portion (and any further portions) add up to 100% of the cumulative total of modafinil particles in the pharmaceutical composition, In one embodiment, a pharmaceutical dosage unit of the present invention contains an effective amount of modafinil, wherein at least about 5% to about 30% of the cumulative total of modafinil particles are smaller than or equal to about 10 microns in diameter and more than about 5% of the total cumulative particles are large particles, having a diameter of more than 220 microns. In another embodiment, at least about 10% to 30% of the cumulative total of modafinil particles are smaller than or equal to about 10 microns in diameter. In still another embodiment, at least about 15% to 30% of the cumulative total of modafinil particles are smaller than or equal to about 10 microns in diameter. In yet another embodiment, at least about 20% to about 30% of the cumulative total of modafinil particles are smaller than or equal to about 10 microns in diameter. And in another embodiment, at least about 25% to about 30% of the cumulative total of modafinil particles are smaller than or equal to about 10 microns in diameter.

In one embodiment, a pharmaceutical dosage unit of the present invention contains an effective amount of modafinil, wherein at least about 5% to about 30% of the cumulative total of modafinil particles are smaller than or equal to about 15 microns in diameter and more than about 5% of the total cumulative particles are more than 220 microns in diameter. In another embodiment, at least about 10% to 30% of the cumulative total of modafinil particles are smaller than or equal to about 15 microns in diameter. In still another embodiment, at least about 15% to 30% of the cumulative total of modafinil particles are smaller than or equal to about 15 microns in diameter. In yet another embodiment, at least about 20% to about 30% of the cumulative total of modafinil particles are smaller than or equal to about 15 microns in diameter. In another embodiment, at least about 25% to about 30% of the cumulative total of modafinil particles are smaller than or equal to about 15 microns in diameter.

In yet another embodiment, a pharmaceutical dosage unit of the present invention contains an effective amount of modafinil, wherein at least about 5% to about 30% of the cumulative total of modafinil particles are smaller than or equal to about 20 microns in diameter and more than about 5% of the total cumulative particles are more than 220 microns in diameter. In another embodiment, at least about 10% to 30% of the cumulative total of modafinil particles are smaller than or equal to about 20 microns in diameter. In still another embodiment, at least about 15% to 30% of the cumulative total of modafinil particles are smaller than or equal to about 20 microns in diameter. In yet another embodiment, at least about 20% to about 30% of the cumulative total of modafinil particles are smaller than or equal to about 20 microns in diameter. An in another embodiment, at least about 25% to about 30% of the cumulative total of modafinil particles are smaller than or equal to about 20 microns in diameter.

In yet another embodiment, a pharmaceutical dosage unit of the present invention contains an effective amount of modafinil, wherein at least about 5% to about 30% of the cumulative total of modafinil particles are smaller than or equal to about 25 microns in diameter and more than about 5% of the total cumulative particles are more than 220 microns in diameter. In another embodiment, at least about 10% to 30% of the cumulative total of modafinil particles are smaller than or equal to about 25 microns in diameter. In still another embodiment, at least about 15% to 30% of the cumulative total of modafinil particles are smaller than or equal to about 25 microns in diameter. In yet another embodiment, at least about 20% to about 30% of the cumulative total of modafinil particles are smaller than or equal to about 25 microns in diameter. An in another embodiment, at least about 25% to about 30% of the cumulative total of modafinil particles are smaller than or equal to about 25 microns in diameter.

In still another embodiment of the invention, a pharmaceutical dosage unit (including a tablet, pill or capsule of modafinil) contains modafinil particles wherein about 5% to about 35% of the total cumulative number of particles are more than 220 microns in diameter. In other embodiments, typically between about 10% to 30%, more typically 15% to 30%, and in some embodiments between 20% to 30% and even 25% to 30% of the cumulative total of particles have diameters larger than 220 microns in diameter. Further, in such dosage units, the total amount of modafinil can be about 10 milligrams to about 800 milligrams, more typically about 15 milligrams to about 800 milligrams, and in other embodiments the total amount of modafinil in the dosage unit can be at least about 100 milligrams to about 200 milligrams. In preferred embodiments, dosage units contain 100 milligrams or 200 milligrams of modafinil.

The total weight of modafinil in the pharmaceutical composition, containing at least the first portion and optionally additional portions of modafinil from discrete lots, as described above, can include between about 10 milligrams to about 800 milligrams of modafinil, more typically between about 15 milligrams and about 800 milligrams, preferably between about 50 to 400 milligrams and most preferably between about 100 milligrams to 200 milligrams of modafinil.

In embodiments wherein the modafinil is in a unit dose form, a pharmaceutical composition of the present invention can contain between about 10 milligrams and about 800 milligrams of modafinil, more typically between about 15 milligrams and about 800 milligrams, preferably between about 50 to about 400 milligrams and most preferably between about 100 milligrams to about 200 milligrams of modafinil. In unit dose form, embodiments having first and at least second portions, as described above, the first portion of solid particles can be at least 15%, typically at least 50%, more typically at least 90% and in some embodiments at least 99% of the total weight of the total modafinil in the unit dose form.

Although primarily described herein with respect to "cumulative total number of particles," it is within the ability of one skilled in the art to also make blends based upon weight of the portions used from each of the discrete lots, as detailed above. In particular, the density of modafinil is about 0.50 grams per cubic centimeter (bulk density) and about 0.60 grams per cubic centimeter (tap density). Using the density information, the statistical information that is described herein, and assuming the particles of modafinil are spherical, accurate determinations of the appropriate weight of particles in each discrete lot can be made. Similar calculations can be made with respect to the surface area of the particles.

Notwithstanding similar dissolution and/or bioequivalence to approved modafinil products, compositions including more than about 5% large or very large particles should be carefully tested, preferably in human clinical trials, in order to verify safety in humans.

Methods of Treatment

Although the specific examples presented herein are directed to modafinil of a defined particle size, other uses of modafinil (e.g., for treatment of Parkinson's disease, urinary incontinence, Alzheimer's disorder, etc.) have been presented in the art, and those utilities are appropriate in conjunction with the invention as disclosed herein.

Accordingly, the present invention also includes a method of altering the somnolent state of a mammal, such as a human, by administering to the mammal an effective amount of the composition of the present invention.

Furthermore, the present invention includes a method for enhancing alertness or increasing regularity of sleep rhythms by administering an effective amount of a composition of the present invention.

The present invention also includes within its scope a method of treating a mammal diagnosed with a modafinil-responsive disease or condition, including, but not limited to, narcolepsy, sleepiness, excessive sleepiness, excessive daytime sleepiness associated with narcolepsy, Parkinson's disease, urinary incontinence, multiple sclerosis fatigue, ADHD, Alzheimer's disorder, sleep apnea, obstructive sleep apnea, depression, and ischemia, by administering an amount of modafinil, as one or more oral unit doses, wherein the unit doses contain an effective amount of the composition of the present invention.

EXAMPLES

Example 1

Separation of a Batch of Modafinil Into Discrete Lots

A bulk batch of modafinil is prepared in a conventional manner having a particle size distribution of between about 10 microns and 500 microns. The particles of the bulk batch pass through a series of particle separation screens having screen opening diameters of 440 microns, 300 microns, 220 microns, 100 microns, 30 microns, 20 microns, and 10 microns. After the 10 microns screen, there is a holding container to contain any particles of modafinil that pass through the 10 micron screen. The modafinil passes through the screens in order of decreasing diameter. The screens are designed to retain a portion of modafinil that cannot pass through the screen openings.

The portions are then placed into an appropriate container. Labels on each container indicate the particle diameter of the contents. The first container has a label "larger than or equal to 440 microns." The second container has a "smaller than 440 microns and larger than or equal to 300 microns." The third container has a label "smaller than 300 microns and larger than or equal to 220 microns." The fourth container has a label "smaller than 220 microns and larger than or equal to 100 microns." The fifth container has a label "smaller than 100 microns and larger than or equal to 30 microns." The sixth container has a label "smaller than 30 microns and larger than or equal to 20 microns." The seventh container has a label "smaller than 20 microns and larger than or equal to 10 microns." The eighth container has a label "smaller than 10 microns."

Example 2

Pharmaceutical Compositions From Discrete Lots

Combining a first portion from the eighth container of Example 1, a second portion from the sixth container of Example 1, a third portion from the fourth container of Example 1, and a fourth portion from the second container of Example 1 forms a pharmaceutical composition of the present invention.

The first portion contains about 40% of the total cumulative particles of modafinil in the pharmaceutical composition. The second portion contains about 30% of the total cumulative particles of modafinil in the pharmaceutical composition. The third portion contains about 27% of the total cumulative particles of modafinil in the pharmaceutical composition. The fourth portion contains about 3% of the total cumulative particles of modafinil in the pharmaceutical composition. Accordingly, about 97% of the cumulative total of particles in the pharmaceutical composition are smaller than or equal to about 200 microns in diameter. A particle size distribution curve of this example of the present invention is shown in FIG. 2.

Examples 3-42

In the present invention, preferably none, or substantially none, of the particles exceed 600 to 1500 microns in diameter. Specific illustrative examples of the invention include but are not limited to tablets comprising about 100 milligrams of modafinil wherein the modafinil particle size distribution is as follows:

| Particle Size (um) | Ex 3 (%) | Ex 4 (%) | Ex 5 (%) | Ex 6 (%) | Ex 7 (%) | Ex 8 (%) | Ex 9 (%) | Ex 10 (%) | Ex 11 (%) | Ex 12 (%) |
|---|---|---|---|---|---|---|---|---|---|---|
| <=10 | 10 | 10 | 85 | 50 | 20 | 20 | 30 | 40 | 20 | 75 |
| >=200 | 5 | 5 | 15 | 50 | 10 | 10 | 20 | 5 | 60 | 25 |
| <=400 | 100 | 95–100 | 100 | 100 | 100 | 95–100 | 95–100 | 95–100 | 95–100 | 100 |
| | Ex 13 (%) | Ex 14 (%) | Ex 15 (%) | Ex 16 (%) | Ex 17 (%) | Ex 18 (%) | Ex 19 (%) | Ex 20 (%) | Ex 21 (%) | Ex 22 (%) |
| <=15 | 10 | 10 | 85 | 50 | 20 | 20 | 30 | 40 | 20 | 75 |
| >=200 | 5 | 5 | 15 | 50 | 10 | 10 | 20 | 5 | 60 | 25 |
| <=400 | 100 | 95–100 | 100 | 100 | 100 | 95–100 | 95–100 | 95–100 | 95–100 | 100 |
| | Ex 23 (%) | Ex 24 (%) | Ex 25 (%) | Ex 26 (%) | Ex 27 (%) | Ex 28 (%) | Ex 29 (%) | Ex 30 (%) | Ex 31 (%) | Ex 32 (%) |
| <=20 | 10 | 10 | 85 | 50 | 20 | 20 | 30 | 40 | 20 | 75 |
| >=200 | 5 | 5 | 15 | 50 | 10 | 10 | 20 | 5 | 60 | 25 |
| <=400 | 100 | 95–100 | 100 | 100 | 100 | 95–100 | 95–100 | 95–100 | 95–100 | 100 |
| | Ex 33 (%) | Ex 34 (%) | Ex 35 (%) | Ex 36 (%) | Ex 37 (%) | Ex 38 (%) | Ex 39 (%) | Ex 40 (%) | Ex 41 (%) | Ex 42 (%) |
| <=25 | 10 | 10 | 85 | 50 | 20 | 20 | 30 | 40 | 20 | 75 |
| >=200 | 5 | 5 | 15 | 50 | 10 | 60 | 15 | 30 | 60 | 5 |
| <=400 | 100 | 95–100 | 100 | 100 | 100 | 90 | 50 | 70 | 95 | 90 |

Example 43

Dissolution

Modafinil is separated into two discrete lots having particle diameters larger than or equal to about 250 microns in one discrete lot and smaller than or equal to about 200 microns in the second discrete lot. A portion of the second discrete lot (smaller than or equal to 200 microns) is further separated into three discrete lots: (a) between 0 microns and 10 microns, (b) between 10 microns and 100 microns, and (c) between 100 microns and 200 microns in diameter. Two blends are prepared using the discrete lots, one blend having 80% particles between 10 microns and 100 microns and 20% particles larger than about 250 microns in diameter. The second blend contains 60% particles smaller than or equal to about 200 microns, and 40% particles having diameters larger than or equal to about 250 microns in diameter. Portions of the blends are further combined with SDS (sodium dodecyl sulfate), as detailed below, and are then formed into tablets. In vitro comparative dissolution studies are then performed on the tablets.

As shown in FIG. 3, the dissolution profile of the FDA approved 100 milligram tablet of Provigil® (modafinil) was compared with tablets of modafinil wherein 80% of the particles in the tablet were between about 10 microns and 100 microns in diameter, and 20% particles were larger than about 250 microns in diameter. The three comparison tablets contained either no SDS, 0.2% SDS or 0.5% SDS, by weight, as shown in FIG. 3. The results of the dissolution experiment shown in FIG. 3 indicate that in some embodiments the greater the amount of SDS in the tablet, the closer the dissolution curves of the blends approximated the curve of the FDA approved tablet of Provigil® (modafinil).

DEFINITIONS

"Particle," as used herein, refers to a primary physical unit or an aggregated physical unit of the acetamide compound, i.e., a piece or a grain of acetamide.

As used herein, the term "mean," when used in reference to the size of modafinil particles, refers to the sum of the size measurements of all measurable particles measured divided by the total number of particles measured. For example, for five measurable particles which could be measured, and were determined to have diameters of 20 microns, 23 microns, 20 microns, 35 microns and 20 microns, the mean diameter would be 23.6 microns. As used herein, the statistical term "average" is synonymous with the term "mean."

As used herein, the term "diameter" is a volumetric measurement based on the theoretical spherical shape of a modafinil particle. Specifically, the volume of a theoretically spherical particle of modafinil can be defined by: Volume $(V)=(4/3)\cdot\pi\cdot r^3$. Therefore, the theoretical diameter can be defined by: Diameter $(D)=2\cdot(3\cdot V/4/\pi)^{1/3}$. Similarly, the surface area of a particle can also be determined from the diameter of the theoretically spherical particle by the equation: Surface Area $(SA)=4\cdot\pi\cdot(0.5\cdot D)^2$.

As used herein, "about" means plus or minus ten percent of the indicated value, such that "about 20 microns" indicates 18 to 22 microns. The size of the particle can be determined, e.g., by the methods provided below, and by other conventional methods known to those of skill in the art.

As used herein, the term "small particles" refers to particles having diameters smaller than or equal to about 200 microns. As used herein the term "large particles" refers to particles that are larger than 220 microns in diameter and smaller than or equal to about 400 microns. As used herein, the term "very large particles" refers to particles having a diameter larger than 440 microns.

As used herein, "consisting essentially of" refers to excluding other active ingredients but including excipients and additional amounts of the active ingredient to account for degradation or otherwise.

The expression "bioequivalent" or "bioequivalence" is a term of art and is intended to be defined in accordance with Approved Drug Products with Therapeutic Equivalence Evaluations, 22nd Edition, which is published by the U.S. Department of Health and Human Services, and is commonly known as the "Orange Book". Generally, bioequivalence can be defined as the absence of significant difference in the rate and extent to which the active ingredient or active moiety in pharmaceutical equivalents or pharmaceutical alternatives becomes available at the site of drug action when administered at the same molar dose under similar conditions in an appropriately designed study. Bioequivalence of different formulations of the same drug substance involves equivalence with respect to the rate and extent of drug absorption. The extent and rate of absorption of the test formulation is compared to a reference formulation in order to determine whether the two formulations are bioequivalent. The standard bioequivalence study is conducted in crossover fashion by extensive testing which includes administering single doses of the test and reference drugs to a number of volunteers, usually 12 to 24 healthy normal adults, and then measuring the blood or plasma levels of the drug over time. The pharmacokinetic characteristics of the concentration-time curve, such as the maximum observed plasma concentration ($C_{max}$), the time to reach $C_{max}$, and the area under the plasma concentration versus time curve (AUC), are examined by statistical procedures which are well-established in the field of pharmacokinetics. Two formulations whose rate and extent of absorption differ by −20%/+25% or less are generally considered to be bioequivalent. Detailed guidelines for establishing the bioequivalence of a formulation with a reference formulation have been published by the FDA Office of Generic Drugs, Division of Bioequivalence.

An "effective amount," as used herein, is an amount of modafinil that is effective for treating a somnolent or somnolescent state, i.e., an amount of modafinil that is able to reduce or eliminate the symptoms of a somnolescent state. An effective amount of a pharmaceutical composition of the invention is useful for enhancing alertness, or increasing regularity of sleep rhythms.

A "pharmaceutical composition," as used herein, means a medicament for use in treating a mammal that comprises modafinil prepared in a manner that is appropriate for administration to a mammal. A pharmaceutical composition according to the invention may also, but does not of necessity, include a non-toxic pharmaceutically acceptable carrier. A pharmaceutical composition can also include bulk modafinil particles of the present invention for use in preparing dosage units.

As used herein, the term "bounded" refers to the upper and lower limits of modafinil particle diameters. For example, a discrete lot of modafinil particles in which substantially all of the particles have a diameter of 10 to 50 microns has a bounded particle size range of 10 to 50 microns.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations. Further, the contents of all references cited herein are hereby incorporated by reference.

What is claimed is:

1. A method of formulating a composition of modafinil comprising the steps of:
   a) providing a batch of modafinil, wherein the particles in the batch have a distribution of particle diameters;
   b) separating the particles in the batch of modafinil into at least two discrete lots of modafinil particles, thereby forming at least a first discrete lot and a second discrete lot, wherein the particle size distribution of the modafinil particles in the second discrete lot is different than the particle size distribution of the modafinil particles in the first discrete lot such that at least about 95% of the particles in the first lot and at least about 95% of the particles in the second lot do not overlap in size;
   c) blending a portion of the first lot with a portion of the second lot; and
   d) forming a composition of modafinil from the blend of the first lot and the second lot;
wherein the proportions of the first discrete lot and the second discrete lot are adjusted so that between about 10% to about 30% by weight of the modafinil particles in the composition have diameters greater than 220 microns.

2. The method of claim 1, wherein the proportions of the first lot and the second lot are adjusted so that fewer than about 85% by weight of the modafinil particles in the composition have diameters smaller than about 200 microns.

3. The method of claim 1, wherein the proportions of the first lot and the second are adjusted so that fewer than about 75% by weight of the particles in the composition have diameters smaller than 200 microns.

4. The method of any one of claim 1, 2 or 3, further comprising the step of forming said composition into an oral dosage unit.

5. The method of claim 4 wherein said oral dosage unit releases at least 80% of the modafinil in 45 minutes in a 0.1 N HCl solution.

6. The method of claim 4 wherein said oral dosage unit contains 100 mg of modafinil, and is bioequivalent to a 100 mg modafinil dosage unit in which at least about 95% of the particles are smaller than about 200 microns.

7. The method of claim 1, wherein about 95% by weight of the modafinil particles in the first discrete lot have a particle diameter of less than 200 microns and about 95% by weight of the modafinil particles in the second discrete lot have a particle diameter of more than 220 microns and less than 400 microns.

* * * * *